US010388988B2

(12) United States Patent
Schmidt

(10) Patent No.: US 10,388,988 B2
(45) Date of Patent: *Aug. 20, 2019

(54) SALT OF BICYCLIC AROMATIC ANIONS FOR LI-ION BATTERIES

(71) Applicant: Arkema France, Colombes (FR)

(72) Inventor: Grégory Schmidt, Mornant (FR)

(73) Assignee: ARKEMA FRANCE, Colombes (FR)

( * ) Notice: Subject to any disclaimer, the term of this patent is extended or adjusted under 35 U.S.C. 154(b) by 963 days.

This patent is subject to a terminal disclaimer.

(21) Appl. No.: 14/400,165

(22) PCT Filed: Apr. 25, 2013

(86) PCT No.: PCT/FR2013/050926
§ 371 (c)(1),
(2) Date: Nov. 10, 2014

(87) PCT Pub. No.: WO2013/182767
PCT Pub. Date: Dec. 12, 2013

(65) Prior Publication Data
US 2015/0111096 A1   Apr. 23, 2015

(30) Foreign Application Priority Data
Jun. 4, 2012   (FR) ...................................... 12 55152

(51) Int. Cl.
*H01M 10/0567* (2010.01)
*C07D 401/04* (2006.01)
*H01M 10/0525* (2010.01)
*H01M 10/0568* (2010.01)

(52) U.S. Cl.
CPC ...... *H01M 10/0567* (2013.01); *C07D 401/04* (2013.01); *H01M 10/0525* (2013.01); *H01M 10/0568* (2013.01); *H01M 2300/0025* (2013.01)

(58) Field of Classification Search
None
See application file for complete search history.

(56) References Cited

U.S. PATENT DOCUMENTS 5,109,012 A   4/1992  Willis et al.
6,548,212 B1*  4/2003  Heider .............. H01M 10/0525
                                                    252/62.2
2004/0009393 A1   1/2004  Kim et al.
2005/0042713 A1*  2/2005  Thompson ............... C07K 1/12
                                                    435/68.1
2011/0229769 A1*  9/2011  Ihara ................... B60L 11/1879
                                                    429/325
2011/0311884 A1  12/2011  Armand et al.
2015/0126746 A1   5/2015  Schmidt

FOREIGN PATENT DOCUMENTS

| CN | 102195083 A | 9/2011 |
| CN | 102264926 A | 11/2011 |
| JP | H 3 83981 | 4/1991 |
| JP | 2011 19508 A | 2/2011 |
| JP | 2012 500833 A | 1/2012 |
| WO | WO 2010/023413 A1 | 3/2010 |

OTHER PUBLICATIONS

U.S. Appl. No. 14/400,189, Grégory Schmidt, filed Nov. 10, 2014.
U.S. Appl. No. 14/400,189, Schmidt.
Schmidt, U.S. Appl. No. 14/400,189, entitled "Salt of Bicyclic Aromatic Anions for Li-Ion Batteries," filed Nov. 10, 2014.
Niedzicki L. et al. "New type of imidazole based salts designed specifically for Li ion batteries", Electrochimica Acta, vol. 55, No. 4, 2010, pp. 1450-1454.
Scheers J. et al. "Benzimidazole and imidazole lithium salts for battery electrolytes", Journal of Power Sources, vol. 195, No. 18, 2010, pp. 6081-6087.
Office Action (Notice of Reasons for Rejection) dated Sep. 13, 2016, by the Japanese Patent Office in Japanese Patent Application No. 2015-514550 (4 pages).
International Search Report (PCT/ISA/210) dated Jul. 16, 2013, by the French Patent Office as the International Searching Authority for International Application No. PCT/FR2013/050926.
Official Action issued in Chinese Patent Application No. 201380028835.1, dated Oct. 10, 2015, The State Intellectual Property Office of People's Republic of China, 8 pages (English-language translation), 5 pages (CN Official Action).
Baldwin, J.J., et al., "2-Pyridylimidazoles as inhibitors of Xanthine Oxidase," *Journal of Medicinal Chemistry*, 1977, pp. 1189-1193, vol. 20, No. 9, The American Chemical Society, USA.

* cited by examiner

*Primary Examiner* — Eli S Mekhlin
(74) *Attorney, Agent, or Firm* — Buchanan Ingersoll & Rooney P.C.

(57) ABSTRACT

Salts of bicyclic imidazole compounds (IV) having general structural formulae in which A represents a monovalent cation, X represents independently a carbon atom, an oxygen atom, a sulphur atom or a nitrogen atom. Also, an associated production method and a use thereof, in particular as an electrolyte component for batteries.

20 Claims, No Drawings

SALT OF BICYCLIC AROMATIC ANIONS FOR LI-ION BATTERIES

FIELD OF THE INVENTION

The present invention relates to bicyclic imidazole compounds and their salts, to their processes of manufacture and to their uses, in particular as electrolyte component for batteries.

TECHNICAL BACKGROUND

A lithium-ion or sodium-ion battery comprises at least one negative electrode, one positive electrode, one separator and one electrolyte. The electrolyte is composed of a lithium or sodium salt dissolved in a solvent, which is generally a mixture of organic carbonates, in order to have a good compromise between the viscosity and the dielectric constant.

The most widely used salts include lithium hexafluorophosphate ($LiPF_6$), which has many of the numerous qualities required but exhibits the disadvantage of decomposing in the form of hydrogen fluoride gas. This presents safety problems, in particular in the context of the impending use of lithium-ion batteries in specific vehicles.

The prerequisite for having an electrolyte salt is good chemical dissociation between the cation and the anion, which implies a negative charge on the anion which is delocalized or reduced by withdrawing effects.

Salts based on the withdrawing effect have thus been developed, such as LiTFSI (lithium bis(trifluoromethanesulfonyl)imide) and LiFSI (lithium bis(fluorosulfonyl)imide).

Other salts, this time based on the delocalization of the charge, have also been developed, such as LiTDI (lithium 4,5-dicyano-2-(trifluoromethyl)imidazolide), as is taught in the document WO 2010/023413. However, the latter exhibit ionic conductivities which are lower than those mentioned above.

The applicant company has discovered that the presence of a second aromatic ring makes it possible to increase the delocalization of the negative charge and to thus increase this ionic conductivity.

SUMMARY OF THE INVENTION

In that which follows:

DAMN denotes diaminomaleonitrile and is represented by the formula (I):

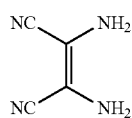

I

The compounds (II) are represented by the expanded general formulae below. They are denoted under (IIa) when the aromatic ring comprises six atoms and under (IIb) for an aromatic ring having five atoms:

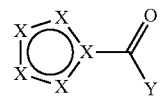

IIa

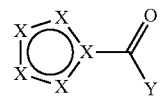

IIb

The bicyclic imidazole compounds (III) are represented by the expanded general formulae below. They are denoted under (IIIa) when the aromatic cycle comprises six atoms and under (IIIb) for an aromatic ring comprising five atoms:

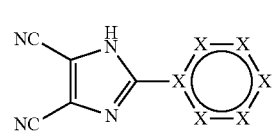

IIIa

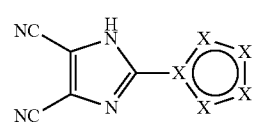

IIIb

The salts of the bicyclic imidazole compounds (IV) are represented by the expanded general formulae below. They are denoted under (IVa) when the aromatic ring comprises six atoms and under (IVb) for an aromatic ring comprising five atoms:

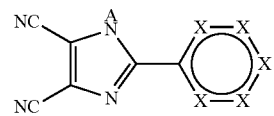

IVa

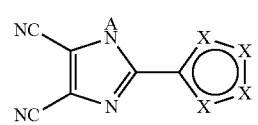

IVb

The compounds (V) are represented by the expanded general formulae below. They are denoted under (Va) when the aromatic ring comprises six atoms and under (Vb) for an aromatic ring comprising five atoms:

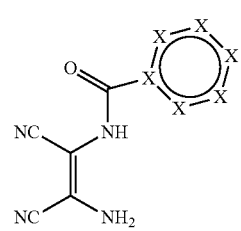

Va

Vb

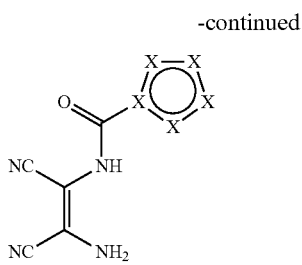

In the general formulae above, A represents a monovalent cation, X independently represents a carbon atom, an oxygen atom, a sulfur atom, a phosphorus atom or a nitrogen atom and Y represents a chlorine atom, an OCORf group, in which Rf represents the same aromatic ring as in the compounds IIa and IIb, or an OR' group, in which R' represents an alkyl group of 1 to 5 carbon atoms optionally substituted by one or more fluorine atoms.

When X represents a carbon or phosphorus or nitrogen atom, the substituents can independently be electron-withdrawing or electron-donating groups defined by a Hammett parameter (the Hammett parameter is a tabulated constant which is determined for a series of substituent groups by measuring the dissociation constant of the corresponding benzoic acids) of between −0.7 and 1.0. Preferably, the substituents are chosen from a cyano (CN) group, an $R_1$ group, an ether group of $OR_1$ type, an amino group of $N(R_1)_2$ type, an ester group of $CO_2R_1$ type, a sulfonyl group of $SO_2R_1$ type or a phosphonyl group of $PO_2R_1$ type, where $R_1$ has the formula $C_nH_mX'_p$ with n between 0 and 6, m between 0 and 13, X' a halogen (F, Cl, Br and I) and p between 1 and 13.

When Y represents a chlorine atom, an OCORf group or an OR' group, the compound (II) is respectively an acyl chloride, a symmetrical anhydride or an ester.

The invention relates first to the bicyclic imidazole compounds (III) and their salts (IV).

The invention relates secondly to the processes for the manufacture of bicyclic imidazole compounds (III) and their salts (IV).

The invention relates thirdly to the use of the compounds of formula (IV).

DETAILED DESCRIPTION OF THE INVENTION

The invention is now described in more detail and without implied limitation in the description which follows.

The salts of the bicyclic imidazole compounds (IV) according to the present invention are represented by the general formula above in which A represents a monovalent cation A, for example an alkali metal.

The preferred alkali metal is chosen from lithium and sodium.

When X in the general formula represents a carbon, phosphorus or nitrogen atom, the salts (IV) can be substituted. The preferred substituents are electron-withdrawing or electron-donating groups, in particular those having a Hammett parameter of between −0.7 and 1.

The electron-withdrawing and electron-donating groups which are particularly preferred can be chosen from a cyano (CN) group, an $R_1$ group, an ether group of $OR_1$ type, an amino group of $N(R_1)_2$ type, an ester group of $CO_2R_1$ type, a sulfonyl group of $SO_2R_1$ type or a phosphonyl group of $PO_2R_1$ type, where $R_1$ has the formula $C_nH_mX'_p$ with n between 0 and 6, m between 0 and 13, X' a halogen (F, Cl, Br and I) and p between 1 and 13.

Preparation of the Salts of the Bicyclic Imidazole Compounds (Bicyclic Imidazolides) and of the Bicyclic Imidazole Compounds The bicyclic imidazolides (IV) can be prepared from the imidazole compounds (III) by reacting the latter with a base AZ, with A having the same meaning as above and Z representing a hydride, hydroxide or carbonate anion. Preferably, AZ is chosen from lithium hydride, lithium carbonate, lithium hydroxide, sodium hydride, sodium carbonate, sodium hydroxide and the combinations of these.

$$III+AZ \rightarrow IV+AH \qquad (1)$$

The compounds (III) can be prepared from DAMN and an aromatic cyclic acid derivative of general formula (II).

The process for the preparation of the bicyclic imidazole compounds (III) comprises (i) a stage of reaction of DAMN of formula (I) with an aromatic cyclic acid derivative of formula (II) at a temperature $T_1$ of between 0 and 80° C., preferably from 10 to 50° C., more preferably from 20 to 30° C., optionally in the presence of a solvent, to give a compound of formula (V), followed (ii) by a stage during which the compound of formula (V) is subjected to a heat treatment at a temperature $T_2$ with $T_2 > T_1$.

$$DAMN+II \rightarrow III+H_2O+YH \qquad (2)$$

$$DAMN+II \rightarrow V+YH \qquad (2\text{-}1)$$

$$V \rightarrow III+H_2O \qquad (2\text{-}2)$$

Preferably, $T_2$ is greater than $T_1$ by at least 10° C., or by at least 20° C., or by at least 30° C., or by at least 40° C., or by at least 50° C., or by at least 60° C., or by at least 70° C.

Preferably, stage (ii) is carried out immediately following the first stage without intermediate purification, simply by modifying the temperature of the reaction mixture, by heating optionally after a transition period, preferably between 1 minute and 2 hours.

Stage (i) is preferably carried out in the presence of a solvent. Any compound which makes it possible to dissolve the reactant(s) can be used as solvent. Mention may be made, by way of indication, of dioxane, toluene, acetonitrile or dimethylformamide.

When stage (i) is carried out in the presence of a solvent, the concentration of DAMN in the reaction medium is preferably from 0.001 to 2 mol/l, more preferably from 0.1 mol/l to 1 mol/l. The molar ratio of the compound (I) to the compound (II) is preferably from 0.25 to 1.5, more preferably from 0.5 to 1.25.

According to a specific embodiment, the temperature $T_2$ corresponds to the boiling point of the solvent used.

The duration of stage (i) is preferably from 1 to 12 hours, more particularly from 1 to 5 hours, for example approximately 2 hours.

Preferably, stage (ii) is carried out in the presence of an acid catalyst, optionally by addition of a carboxylic acid, such as trifluoroacetic acid, acetic acid or benzoic acid, to the reaction medium.

The acid catalyst can be obtained in situ in the reaction medium, in particular when the compound of formula (II) is an anhydride.

The molar ratio of the compound (V) to the catalyst is preferably from 0.5 to 20, more preferably from 1 to 10.

According to one embodiment of the invention, the temperature of the reaction $T_1$ can be constant throughout the first stage, and/or the temperature of the reaction $T_2$ can be constant throughout the second stage.

According to another embodiment of the invention, the temperature is increasing throughout stage (i) and optionally throughout stage (ii) provided that $T_2$ is greater than $T_1$. In other words, the minimum temperature $T_2$ is greater than the maximum temperature $T_1$.

On conclusion of stage (ii), the bicyclic imidazole compound of formula (III) is preferably isolated and purified.

Thus, the reaction medium can be evaporated and imidazole (III) recrystallized from water to be subsequently recovered by filtration. The solid obtained can be dissolved in an aqueous solution of base AZ, preferably a lithium or sodium base, with a concentration ranging from 10 mol/l to the saturation concentration. Once the compound salt of formula (IV) is formed, the solution can undergo several treatments with active charcoal. The solution can subsequently be evaporated to give the salt of formula (IV).

Preparation of an Electrolyte

The compounds of formula (IV) can be used in the preparation of an electrolyte by dissolving them in an appropriate solvent.

The solvent can be composed of at least one compound chosen from carbonates, glymes, nitriles and sulfones.

Mention may in particular be made, as carbonate, of ethylene carbonate, glycerol carbonate, dimethyl carbonate, ethyl methyl carbonate, diethyl carbonate or propylene carbonate.

Mention may in particular be made, as glymes, of ethylene glycol dimethyl ether, diethylene glycol dimethyl ether, dipropylene glycol dimethyl ether, diethylene glycol diethyl ether, triethylene glycol dimethyl ether, diethylene glycol dibutyl ether, tetraethylene glycol dimethyl ether and diethylene glycol t-butyl methyl ether.

Mention may in particular be made, as nitriles, of acetonitrile, propionitrile, butyronitrile, methoxypropionitrile, isobutyronitrile and the fluorinated compounds deriving from the above compounds.

Mention may in particular be made, as sulfones, of dimethyl sulfone, sulfolane, ethyl methyl sulfone, propyl methyl sulfone, isopropyl methyl sulfone, isopropyl ethyl sulfone, tert-butyl ethyl sulfone, tert-butyl methyl sulfone and tert-butyl propyl sulfone.

The solvent is preferably composed of a mixture of compounds, advantageously from 2 to 5, chosen from the abovementioned carbonates and/or glymes and/or sulfones.

The proportions by weight of each of the compounds constituting the solvent are preferably between 1 and 10, with respect to the constituent in smallest amount, more preferably between 1 and 8.

The concentration of compound of formula (IV) in the electrolyte is preferably from 0.1 mol/l to 5 mol/l, more preferably from 0.2 mol/l to 2.5 mol/l. Preferably, the electrolyte is composed of a mixture of at least two lithium salts chosen from the imidazolide salt (IV), $LiPF_6$, $LiBF_4$, $CF_3COOLi$, $CF_3SO_2Li$, LiTFSI (lithium bis(trifluoromethanesulfonyl)imide), LiFSI (lithium bis(fluorosulfonyl)imide), LiTDI (lithium 4,5-dicyano-2-(trifluoromethyl)imidazolide) and LiPDI (lithium 4,5-dicyano-2-(pentafluoroethyl)imidazolide). The amount of each lithium salt present in the mixture can vary within wide limits and generally represents between 0.1% and 99.9% by weight, with respect to the total weight of the salts present in the mixture, preferably between 1% and 99% by weight.

Example

The following example illustrates the invention without limiting it.

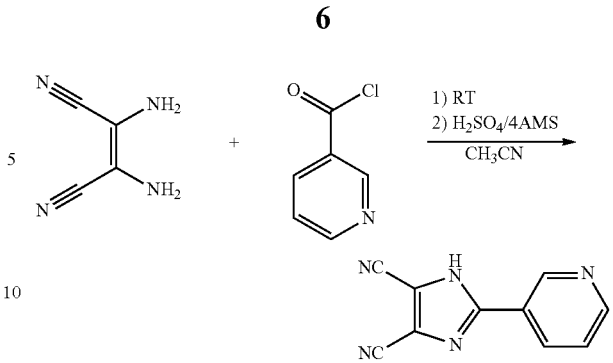

A solution of 1.82 g of nicotinoyl chloride in 25 ml of acetonitrile is added dropwise to a solution of 1.32 g of DAMN in 20 ml of acetonitrile. An abovementioned salmon pink then appears. The 4 A molecular sieve and a few drops of sulfuric acid are subsequently added. The mixture is then heated at reflux for 36 hours. The reaction medium is filtered (removal of the molecular sieve) and is subsequently evaporated. The imidazole is then recrystallized in water and is subsequently recovered by filtration. The solid obtained is dissolved in a saturated aqueous lithium carbon solution. Once the salt has formed, the solution is subjected to five treatments with active charcoal (5 g). The solution is subsequently evaporated to give the lithium salt of the imidazolide.

The invention claimed is:

1. A salt of a bicyclic imidazole compound (IV) represented by expanded general formulae below:

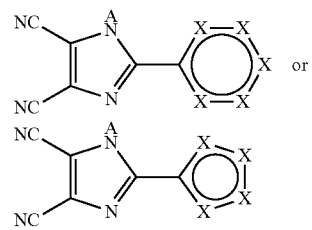

in which A represents a monovalent cation and X independently represents a carbon atom, an oxygen atom, a sulfur atom, a phosphorus atom or a nitrogen atom, wherein at least one X is N.

2. The salt as claimed in claim 1, wherein the monovalent cation A is an alkali metal.

3. The salt as claimed in claim 1, wherein X represents a carbon, phosphorus or nitrogen atom.

4. The salt as claimed in claim 3, wherein the carbon or the nitrogen or the phosphorus is substituted by electron-withdrawing or electron-donating groups having a Hammett parameter of between −0.7 and 1.

5. The salt as claimed in claim 4, wherein the electron-withdrawing or electron-donating group is chosen from hydrogen, fluorine, a cyano (CN) group, a trifluoromethyl ($CF_3$) group, a trifluoromethoxy ($OCF_3$) group or a methoxy ($OCH_3$) group.

6. A process for preparation of a salt of a bicyclic imidazole compound as claimed in claim 1, wherein an imidazole compound (III):

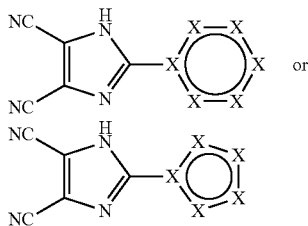

or is reacted with a base AZ, with A having the same meaning as above and Z representing a hydride, hydroxide or carbonate anion.

7. The process as claimed in claim 6, wherein the base AZ is chosen from lithium hydride, lithium carbonate, lithium hydroxide, sodium hydride, sodium carbonate, sodium hydroxide and combinations of these.

8. The process as claimed in claim 6, wherein the imidazole compound (III) is obtained by reacting diaminomaleonitrile with an aromatic cyclic acid derivative of formula (II):

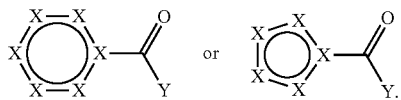

9. The process as claimed in claim 8, comprising (i) a stage of reaction of diaminomaleonitrile with an aromatic cyclic acid derivative of formula (II) at a temperature $T_1$ of between 0 and 80° C., optionally in the presence of a solvent, to give a compound of formula (V):

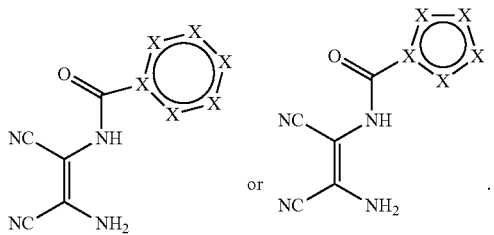

followed (ii) by a stage during which the compound of formula (V) is subjected to a heat treatment at a temperature $T_2$ with $T_2 > T_1$, wherein the heat treatment converts the compound of formula (V) to the imidazole compound (III).

10. The process as claimed in claim 9, wherein the temperature $T_2$ is greater than $T_1$ by at least 10° C.

11. The process as claimed in claim 9, wherein stage (ii) is carried out immediately following the first stage without intermediate purification.

12. The process as claimed in claim 9, wherein stage (i) is carried out in the presence of a solvent.

13. The process as claimed in claim 12, wherein the solvent is chosen from dioxane, toluene, acetonitrile or dimethylformamide.

14. The process as claimed in claim 12, wherein the temperature $T_2$ corresponds to the boiling point of the solvent.

15. The process as claimed in claim 9, wherein stage (ii) is carried out in the presence of an acid catalyst.

16. The process as claimed in claim 15, wherein the acid catalyst is chosen from trifluoroacetic acid, acetic acid or benzoic acid.

17. A battery comprising the salt as claimed in claim 1 as an electrolyte component.

18. The battery as claimed in claim 17, wherein the salt is dissolved in a solvent.

19. An electrolyte composition comprising, in addition to the salt as claimed in claim 1, at least one salt chosen from $LiPF_6$, $LiBF_4$, $CF_3COOLi$, $CF_3SO_2Li$, LiTFSI (lithium bis(trifluoromethanesulfonyl)imide), LiFSI (lithium bis(fluorosulfonyl)imide), LiTDI (lithium 4,5-dicyano-2-(trifluoromethyl)imidazolide) and LiPDI (lithium 4,5-dicyano-2-(pentafluoroethyl)imidazolide).

20. The salt as claimed in claim 1, wherein the bicyclic imidazole compound (IV) is represented by the formula below:

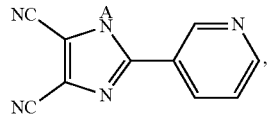

in which A represents a monovalent cation.

* * * * *